(12) United States Patent
Cockman et al.

(10) Patent No.: US 6,953,867 B2
(45) Date of Patent: Oct. 11, 2005

(54) PROCESS FOR THE HYDRATION OF OLEFINS

(75) Inventors: Russell William Cockman, Wallacestone (GB); Gordon John Haining, Grangemouth (GB)

(73) Assignee: Innovene Europe Limited, Middlesex (GB)

( * ) Notice: Subject to any disclaimer, the term of this patent is extended or adjusted under 35 U.S.C. 154(b) by 0 days.

(21) Appl. No.: 10/399,655

(22) PCT Filed: Oct. 19, 2001

(86) PCT No.: PCT/GB01/04669

§ 371 (c)(1),
(2), (4) Date: Apr. 21, 2003

(87) PCT Pub. No.: WO02/32841

PCT Pub. Date: Apr. 25, 2002

(65) Prior Publication Data

US 2004/0044257 A1 Mar. 4, 2004

(30) Foreign Application Priority Data

Oct. 21, 2000 (EP) .......................................... 00122958

(51) Int. Cl.⁷ .................... C07C 41/00; C07C 29/04; C07C 27/08
(52) U.S. Cl. .................. 568/694; 568/695; 568/896; 568/898
(58) Field of Search .................. 568/694, 695, 568/896, 898

(56) References Cited

U.S. PATENT DOCUMENTS

| | | | |
|---|---|---|---|
| 3,311,568 A | 3/1967 | Klimenko et al. | .......... 252/435 |
| 5,208,195 A | 5/1993 | Schlueter et al. | .......... 502/63 |
| 5,959,164 A * | 9/1999 | Lansink-Rotgerink et al. | ... 568/896 |

FOREIGN PATENT DOCUMENTS

| | | |
|---|---|---|
| EP | 0 578 441 A2 | 1/1994 |
| EP | 0 792 859 A2 | 9/1997 |
| EP | 0 941 762 A1 | 9/1999 |

* cited by examiner

*Primary Examiner*—Samuel Barts
*Assistant Examiner*—Sikarl A. Witherspoon
(74) *Attorney, Agent, or Firm*—Nixon & Vanderhye

(57) ABSTRACT

A catalyst support consisting mainly of synthetic silica, with 0.5–10 parts by weight of one or more oxides or phosphates of the elements of group IIA, IIIB, IVB, VB, VIB, VIIB, VIII, IB, IIB, IIIA, IVA and the lanthanides, wherein the support preparation method comprises mixing particulate synthetic silica with particulate oxides or phosphates of the elements of Groups IIA, IIIB, IVB, VB, VIB, VIIB, VIII, IB, IIB, IIIA, IVA and the lanthanides, or with precursors thereof, a forming step and calcinations. The catalyst support is used together with phosphoric acid in the production of alcohols from olefins by hydration.

12 Claims, 5 Drawing Sheets

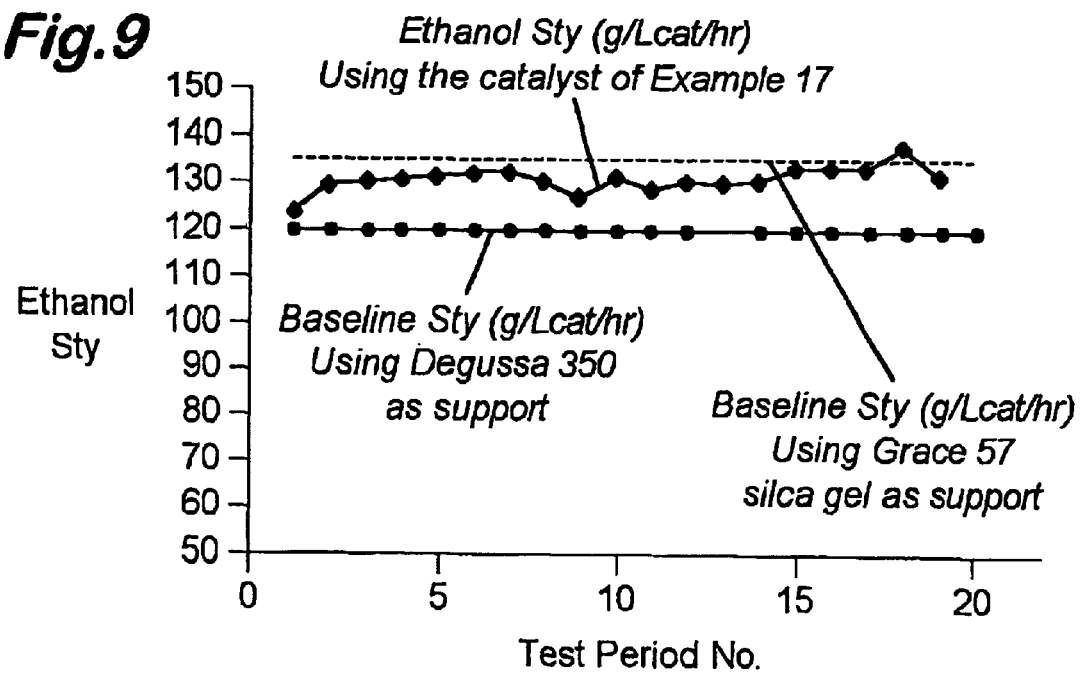
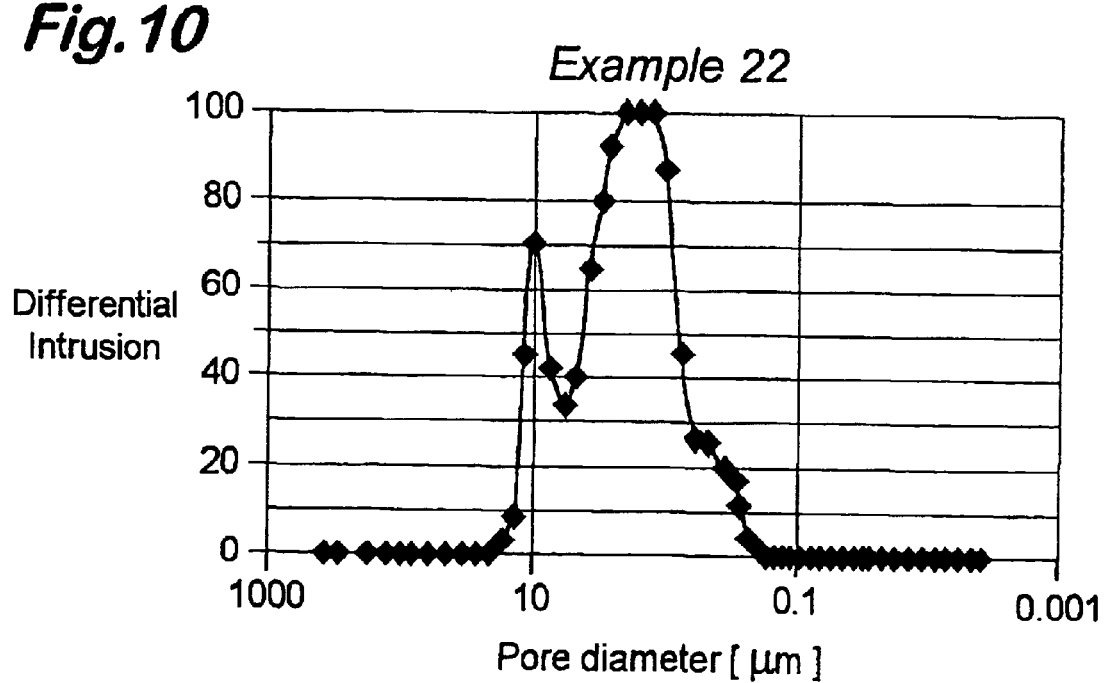

PROCESS FOR THE HYDRATION OF OLEFINS

This application is the U.S. national phase of international application PCT/GB01/04669, filed 19 Oct. 2001, which designated the U.S.

This present invention relates to catalyst supports and in particular, to catalysts supported on such catalyst supports, for use in processes for the hydration of olefins, e.g. in the production of ethanol or isopropanol. The present invention also relates to processes for the hydration of olefins, which employ phosphoric acid supported on such catalyst supports to catalyse the hydration reaction.

Hydration catalysts undergo ageing during operation, which is discernible by a reduction in activity and/or selectivity. Deactivation is frequently due to a reduction in the specific surface area of the support brought about by elevated temperatures. Specific surface area in the context of this application means the BET surface according to well-known method of Brunauer, Emmett and Teller determined by nitrogen adsorption according to DIN 66 132.

The specific surface area of support is closely related to its pore structure. Moreover, solids having a high surface area usually have a completely or predominantly amorphous structure, which has a strong tendency to take on a thermodynamically stable state by crystallite growth accompanied by a reduction in specific surface area. It has been found that catalyst supports containing silicon dioxide are also subject to such ageing. Hydrothermal conditions accelerate ageing. Hydrothermal conditions prevail in chemical reactions in aqueous systems when the temperature is above the boiling point of water and pressure is above standard pressure. It is furthermore known that contaminants, in particular alkali metals, promote the ageing of supports containing silicon dioxide under hydrothermal conditions (c.f. for example R. K. Iler in The chemistry of Silica, page 544, John Wiley & Sons (1979).

EP 0 578 441 B1 describes the use of a catalyst support for the hydration of olefins. The active component, which is brought onto the support by soaking, is phosphoric acid. This particular support comprises of pellets of synthetic silicon dioxide having high crush strength, high porosity and few metallic contaminants. The purpose of the pores of the support is to accommodate the active component. Pore volume is thus preferably greater than 0.8 ml/g. Average pore radius prior to use in the hydration process is in the range between 1 and 50 nm.

In order to achieve optimum hydration performance, EP 0 578 441 B1 specifies a silicon dioxide content of the support of at least 99 wt % with below 1 wt %, preferable below 0.3 wt % of contaminants. This type of catalyst support has also been described in EP 0 393 356 B1 and in U.S. Pat. No. 5,086,031.

It has surprisingly also been found that the catalyst supports based on synthetic pyrogenically produced silicon dioxide described in EP 0 393 356 B1 are also subject to ageing under hydrothermal conditions. Wherein small pores combine to yield larger pores with loss of specific surface area. Initially, pore volume remains virtually unchanged during such ageing. This ageing is unexpected because the pyrogenic silicon dioxide of which the supports consist has excellent temperature resistance according to investigations with a scanning electron microscope, the morphology of pyrogenic silicon dioxide does not change on heating to temperatures of up to 1000° C. for a period of 7 days (Schriftenreihe Pigmente Nr. 11: Grundlage von Aerosil®; Degussa publication, 5th edition, Jun. 1993, page 20).

Klimenko (U.S. Pat. No. 3,311,568) has described the positive influence of $TiO_2$ on the lifetime of a phosphoric acid loaded, naturally occurring siliceous support in the hydration of unsaturated hydrocarbons. At that time it was believed that natural siliceous deposits such as diatomite, kieselguhr or diatomaceous earth were the most suitable supports for these applications. However, naturally occurring siliceous materials always contain impurities that have some adverse effects on the catalytic properties. These adverse affects can be diminished, as is demonstrated in a number of patents, e.g. DE 37 09 401 A1, EP 0 018 022 B1, DE 29 29 919, DE 29 08 491, DE 1 156 772. This, however, requires a substantial number of additional steps in the support/catalyst preparation.

In order to obtain a sufficient physical strength, Klimenko had to calcine at a temperature from 1050 to 1350° C., the calcination time being between 5 and 24 hours. Schluechter et al. (U.S. Pat. No. 5,208,195) recognise that H3PO4 containing catalysts based on synthetic silica-gels supports are highly active and possess a sufficient initial mechanical strength. However, as they state, these supports have the remaining disadvantage that the amorphous silica partially crystallises during prolonged use under conditions of the hydration reaction. This is associated with a sharp decrease in the specific surface area and hence in catalytic activity and with a decrease in mechanical strength. Because of these drawbacks, they prefer to work with naturally based siliceous materials which require a large number of preparation steps, e.g. treatment with acid in order to decrease the alumina content, until they are fit to be used as a support for hydration purposes.

Schluechter et al. describe the use of titanium dioxide in order to increase the compressive strength of catalysts spheres which are largely based on an essentially montmorillonite-containing clay, hence, a natural occurring material. The titanium dioxide is admixed with the acid treated clay and finely divided silica gel, the $TiO_2$ content is 1.5 to 2.5 parts by weight, the content of synthetically produced silica gel is from 20 to 40 parts by weight. The mixture is optionally shaped and calcined. It is also known from the prior art that silica which is modified by impregnation with a soluble Group IVB-compound, shows improved stability, see e.g. EP 0 792 859 A2. Titanium is one of the elements of Group IVB. The silica support is modified with the stabilising element using the impregnation process, preferably by pore volume impregnation.

Pore volume impregnation is performed by dissolving a soluble compound of the stabilising element in a volume of solvent which is equal to the pore volume of the catalyst support and then distributing the solution, for example by spraying, over the support, which may be rotated in a pill coater during spraying in order to ensure uniform impregnation.

Both aqueous and organic solvents or mixtures thereof may be used for impregnation. In industrial practice, water is generally preferred as solvent. Selection of the suitable solvent, however, is dependent upon the stabilising element compound to be used. An organic titanium compound, such as for example tetrabutoxytitanium $(Ti(C_4H_9O)_4$, may also be used instead of aqueous titanium (III) chloride. In this case, butanol is a suitable solvent.

EP 0 792 859 (A2) shows that the degree of stabilisation of pyrogenic silica increases with increasing Ti-content. However, the addition of titanium leads to a decrease in pore volume, and, hence, a lower activity of the catalyst. Therefore, the need exists to keep the Ti-content as low as possible.

As is shown in the examples of the above mentioned patent application, the impregnation with aqueous solutions of TiCl₃ yields materials with only limited stabilisation. At a comparable Ti-loading, the use of a Ti-alcoholate gave much better results. These are thus clearly preferred as source for Ti. Since Ti-alcoholates cannot be dissolved in water, organic solvents have to be used in order to impregnate the stabilising element. Appropriate and costly precautions must be taken to avoid any explosion hazard in the manufacturing of the support.

The modification of supports by means of impregnation with a stabilising element requires a substantial number of steps before the finished stabilised support is obtained. First of all, the support must be shaped, for instance by extrusion or by tabletting, then dried and calcined. Next, the stabilising element needs to be impregnated, then dried again. Finally, the treated supports are calcined at temperatures of between 160 and 900° C.

There is a need therefore for a less expensive and less hazardous support preparation method which, at the same time, still gives the required high degree of stabilisation and leads at the same time to a highly active and selective catalyst.

An object of the present invention is accordingly to provide catalyst supports consisting mainly of synthetic silicon dioxide which, in combination with phosphoric acid, exhibit improved ageing resistance when used under hydrothermal conditions and which, at the same time, have excellent activity and selectivity for the hydration of olefins to the corresponding alcohols.

A further object of the present invention are hydration catalysts which are based on the improved supports according to the invention and which have excellent activity and selectivity for the hydration of olefins to the corresponding alcohols. The above and other objects of this invention are achieved by a catalyst support consisting mainly of synthetic silica, with 0.5–10 parts by weight of one or more oxides or phosphates of the elements of group IIA, IIIB, IVB, VB, VIB, VIIB, VIII, IB, IIB, IIIA, IVA and the lanthanides characterised in that the support preparation method comprises mixing particulate synthetic silica with particulate oxides or phospates of the elements of Groups IIA, IIIB, IVB, VB, VIB, VIIB, VIII, IB, IIB, IIIA, IVA and the lanthanides, or with precursors thereof, a forming step and calcination.

The above and other objects of this invention are also achieved by the supported phosphoric acid catalysts wherein the catalyst support, consisting mainly of synthetic silica, is modified by 0.5 to 10 parts by weight titanium dioxide and/or zirconium dioxide based on the total weight of the calcined support, and in which the silica and the titania and/or zirconium dioxide are mixed, preferably, prior to the forming step.

Thus, according to one aspect, the present invention provides a catalyst support consisting mainly of synthetic silica, with 0.5–10 parts by weight of particulate oxides or phospates of the elements of Groups IIA, IIIB, IVB, VB, VIB, VIIB, VIII, IB, IIB, IIIA, IVA and the lanthanides, or with precursors thereof, preferred titania and/or zirconium dioxide characterised in that the support preparation method comprises mixing particulate synthetic silica with particulate oxides or phospates of the elements of Groups IIA, IIIB, IVB, VB, VIB, VIIB, VIII, IB, IIB, IIIA, IVA and the lanthanides, or with precursors thereof, preferred titania and/or zirconium dioxide, a forming step and calcination.

In preferred embodiments of the invention, the catalyst supports comprise silica, titania or zirconium dioxide.

By mixing particulate oxides or phospates of the elements of Groups IIA, IIIB, IVB, VB, VIB, VIIB, VIII, IB, IIB, IIIA, IVA and the lanthanides, or precursors thereof, preferred titania and/or zirconium dioxide with silica in this manner, the particulate oxides or phospates of the elements of Groups IIA, IIIB, IVB, VB, VIB, VIIB, VIII, IB, IIB, IIIA, IVA and the lanthanides, or precursors thereof, preferred titania and/or zirconium dioxide form domains within the structural framework of the calcined support, and is not just a surface coating. Thus, according to another aspect of the present invention, there is provided a catalyst support comprising a structural framework of synthetic silica, which framework contains domains of particulate oxides or phospates of the elements of Groups IIA, IIIB, IVB, VB, VIB, VIIB, VIII, IB, IIB, IIIA, IVA and the lanthanides, or of precursors thereof preferred titania and/or zirconium dioxide, wherein the particulate oxides or phospates of the elements of Groups IIA, IIIB, IVB, VB, VIB, VIIB, VIII, IB, IIB, IIIA, IVA and the lanthanides, or precursors thereof, preferred titania and/or zirconium dioxide, in said domains form 0.5 to 10 parts by weight based on the total weight of the support.

The resulting support has an improved stability against ageing and is substantially easier to produce than any of the materials from the state of the art. Furthermore, it shows excellent activity and selectivity in the hydration of olefins to alcohols. Thus, according to a further aspect, the present invention provides a process for the hydration of olefins, said process comprising reacting an olefin with water in the presence of phosphoric acid supported on one of the catalyst supports described above. Another object of the present invention is the preparation method for these supports. Such a method comprises: mixing particulate silica, with 0.5 to 10 parts by weight of particulate oxides or phospates of the elements of Groups IIA, IIIB, IVB, VB, VIB, VIIB, VIII, IB, IIB, IIIA, IVA and the lanthanides, or with precursors thereof, preferred titania and/or zirconium dioxide, based on the total weight of the support prior to the forming step;
a forming step and
calcining the formed material between 400 and 1050° C.

The method of the present invention is not only much more simple and easier to carry out than the existing manufacturing technologies, but at the same time also gives materials with improved activity and stability, with excellent selectivities.

DETAILED DESCRIPTION OF THE INVENTION

It has now been found, surprisingly, that the stability of phosphoric acid catalysts based on synthetic silica can be increased very substantially when the synthetic particulate silica is physically admixed with particulate oxides or phospates of the elements of Groups IIA, IIIB, IVB, VB, VIB, VIIB, VIII, IB, IIB, IIIA, IVA and the lanthanides, or with precursors thereof, preferred particulate titania and/or zirconium dioxide prior to the forming step.

The silicon dioxide used in accordance with the present invention consists mainly of synthetic silica. Silica gels, precipitated silica's, both produced by wet chemical methods, are suitable synthetic materials. Synthetic silicon dioxide produced by flame hydrolysis, so-called pyrogenic or fumed silicon dioxide, is preferably used. Fumed or pyrogenic silica is offered by Degussa-Huels under the tradename AEROSIL®.

To prepare AEROSIL®, a volatile silicon compound is sprayed into an oxyhydrogen gas flame consisting of hydrogen and air. In most cases compounds like silicon tetrachloride or SiMeCl₃ are used. These substances hydrolyse under the effect of the water produced in the oxyhydrogen gas reaction to give silicon dioxide and hydrochloric acid. The silicon dioxide, after leaving the flame, is introduced into a so-called coagulation zone where the AEROSIL® primary particles and primary aggregates are agglomerated. The product produced in this stage as a type of aerosol is separated from the gaseous accompanying substances in cyclones and then post-treated with moist hot air. As a result of this process, the residual hydrochloric acid content drops to below 0.025%. Since the AEROSIL® at the end of this process is produced with a bulk density of only about 15 g/l, a vacuum compaction process follows, by means of which compacted densities of about 50 g/l or above may be produced.

The particle sizes of the products obtained in this way may be varied by varying the reaction conditions, such as for example the flame temperature, the proportion of hydrogen or oxygen, the amount of silicon tetrachloride, the residence time in the flame or the length of the coagulation zone.

The titanium dioxide used in accordance with the present invention can be of any source, for instance precipitated or fumed titania. Fumed or pyrogenic titanium dioxide is also offered by Degussa-Huels and is produced by flame hydrolysis of volatile Ti-compounds, like e.g. TiCl₄. The process to make pyrogenic or fumed $TiO_2$ is similar to the Aerosil® process described above.

The titanium dioxide can consist of any of its crystalline modification, e.g. anatase or rutile or it can be wholly or partly amorphous. Mixtures of these different phases are also possible.

The zirconium dioxide used in accordance with the present invention can be of any source, for instance precipitated or fumed zirconium dioxide.

Zirconium dioxide which can be used according to this invention is for instance described in Ullmann's Encyclopedia of Industrial Chemistry, 5$^{th}$ Edition, Vol. A28, 543–571 published by VCH-Verlagsgesellschaft and in PhD Thesis from Patrick D. L. Mercera, titled "Zirconia as a support for catalysts" Universiteit Twente, the Netherlands (1991).

Instead of using particulate oxides or phospates of the elements of Groups IIA, IIIB, IVB, VB, VIB, VIIB, VIII, IB, IIB, IIIA, IVA and the lanthanides, preferred particulate titania and/or zirconium dioxide, it is also possible to use one or more of their precursors, that upon calcination are transformed into the corresponding oxide form. For instance, particulate Zr(OH)₄ can be used instead of or in addition to particulate zirconium dioxide.

For use as support for phosphoric acid hydration catalysts, the content of the particulate oxides or phospates of the elements of Groups IIA, IIIB, IVB, VB, VIB, VIIB, VIII, IB, IIB, IIIA, IVA and the lanthanides, or precursors thereof, preferred titanium dioxide and/or zirconium dioxide in the finished support is from 0.5 to 10 wt.-%, preferably from 1 to 9 wt.-%, most preferably from 2.6 to 8 wt.-%, based on the total weight of the support. Too high concentrations lead to loss of activity caused by a reduction in pore volume by formation of Ti- and/or Zr-phosphates. Too low concentrations, on the other hand, lead to an insufficient stabilisation of the catalyst and, hence, a too short lifetime.

The content of synthetic silica in the calcined support can be at last 80%. The support preferably consists of particles with dimensions between 0.8 and 10 mm, most preferably from 1.5 to 8 mm. Too small particles lead to an unacceptable pressure drop over the catalyst bed whereas too large particles result in diffusion limitation and, hence, lower activity of the catalyst. The surface area of the fresh unloaded support is mainly determined by the starting compounds silica and the particulate oxides or phospates of the elements of Groups IIA, IIIB, IVB, VB, VIB, VIIB, VIII, IB, IIB, IIIA, IVA and the lanthanides, or precursors thereof, preferred and titania and/or zirconium dioxide and can be anywhere from 5 to 600 m²/g, preferably from 10 to 400 m²/g.

One of the most important properties of support materials to be used in hydration catalysts is their pore volume. A higher pore volume enables a higher uptake of phosphoric acid and thus leads to a higher activity of the catalyst. The pore volume can be anywhere from 0. 5 to 1.8 ml/g, preferably from 0.8 to 1.5 ml/g, most preferably from 0.9 to 1.5 ml/g.

The support can exist in form of tablets, extrudates, spheres or beads. For extrudates and tablets the standard form is cylindrical, but all other shapes known in the art, e.g. rings, wagon wheels, trilobes, stars, etc. can be used as well. The front and back end of such tablets can either be flat or capped.

The bulk density of the support is determined mainly by the pore volume, the titania and/or zirconium dioxide content and by the form and dimensions of the individual support particles. The bulk density can thus vary within a broad range and can be anywhere from 300 to 800 g/l.

Forming can consist of any forming technique. The preferred forming methods for supports to be used in a fixed bed hydration process are tabletting, compression or extrusion.

In the process of support preparation, particulate synthetic silica in a preferably finely divided form is admixed with particulate oxides or phospates of the elements of Groups IIA, IIIB, IVB, VB, VIB, VIIB, VIII, IB, IIB, IIIA, IVA and the lanthanides, or with precursors thereof, preferred titania and/or zirconium dioxide, also in a preferably finely divided form, together with water and forming additives, like lubricants and/or pore builders. Optionally, silica sol or naturally occurring silica can be added, their maximum content is 10 parts by weight, based on the weight of the calcined support. The mixture is then thoroughly mixed or kneaded. Optionally, the mixture can be dried partially or completely before the forming step, especially in the case of tabletting. The mixture is brought into its final form by the chosen forming technique, e.g. extrusion, tabletting or compression.

Finely divided in this respect means that the silica and the particulate oxides or phospates of the elements of Groups IIA, IIIB, IVB, VB, VIB, VIIB, VIII, IB, IIB, IIIA, IVA and the lanthanides, or precursors thereof, preferred titania and/or zirconium dioxide, prior to the mixing or kneading step consist of agglomerates preferably in the range of up to 100 µm, more preferably up to 50 µm. Agglomerates that are in this range, should be so loosely bound that they, in the mixing or kneading step, are reduced in size to such an extent that the final support comprises small domains of particulate oxides or phospates of the elements of Groups IIA, IIIB, IVB, VB, VIB, VIIB, VIII, IB, IIB, IIIA, IVA and the lanthanides, or of precursors thereof preferred titania and/or zirconium dioxide.

Because the forming procedure includes physically admixing particulate silica and particulate oxides or phospates of the elements of Groups IIA, IIIB, IVB, VB, VIB, VIIB, VIII, IB, IIB, IIIA, IVA and the lanthanides, or precursors thereof, preferred titania and/or zirconium dioxide, the finished support contains domains of particulate oxides or phospates of the elements of Groups IIA, IIIB, IVB, VB, VIB, VIIB, VIII, IB, IIB, IIIA, IVA and the lanthanides, or of precursors thereof preferred titania and/or zirconium dioxide. The size and the distribution of these domains throughout the formed support are important with respect to the stability. After the mixing or kneading procedure in conjunction with the forming step, e.g. extrusion or tabletting, and calcination, 50% or more of the domains of particulate oxides or phospates of the elements of Groups IIA, IIIB, IVB, VB, VIB, VIIB, VIII, IB, IIB, IIIA, IVA and the lanthanides, or precursors thereof preferred titania and/or zirconium dioxide, in the calcined support are smaller than 2 μm in size. Preferably, at least 50% of the domains of particulate oxides or phospates of the elements of Groups IIA, IIIB, IVB, VB, VIB, VIIB, VIII, IB, IIB, IIIA, IVA and the lanthanides, or precursors thereof, preferred titania and/or zirconium dioxide is smaller than 1 μm and more preferably, at least 50% of the domains of particulate oxides or phospates of the elements of Groups IIA, IIIB, IVB, VB, VIB, VIIB, VIII, IB, IIB, IIIA, IVA and the lanthanides, or precursors thereof, preferred titania and/or zirconium dioxide is in the range below 0.8 μm. Most preferably, at least 90% of the domains of particulate oxides or phospates of the elements of Groups IIA, IIIB, IVB, VB, VIB, VIIB, VIII, IB, IIB, IIIA, IVA and the lanthanides, or precursors thereof, preferred titania and/or zirconium dioxide is in the range below 0.8 μm.

Forming additives can be all aids known in the art, they may for instance have a binding or a lubricating or a pore building function. Examples are cellulose and its derivatives, polyethylene glycol, wax, ammonia or ammonia releasing compounds, polyvinylalcohols, starch, sugars, etc.

The contents of the different substances in the mixture is to be adjusted such that the consistency of the mixture is suitable for the chosen forming technique. Optionally, the mixture can be dried partially or completely before the forming step.

After the forming step, the shaped bodies are optionally dried and then calcined. Whereas drying is normally carried out at temperatures below 200° C., calcination takes place preferably between 400 and 1050° C., most preferably between 450 and 1000° C. High calcination temperatures are no problem since the support materials according to this invention have surprisingly good thermal stability. The duration of the calcination can be anywhere from 15 minutes to several hours, depending on the type and size of kiln in which the calcination is carried out. The calcination is preferably carried out in air.

The catalyst supports as described herein are particularly advantageous for hydrating olefins to produce lower alkanols. For the hydration of olefins, phosphoric acid is introduced into the catalyst support as the active component. To this end, once the stabilised support has been calcined, it may be loaded with an aqueous solution of phosphoric acid. The phosphoric acid solution may contain 15 to 85 wt. % of phosphoric acid relative to the total weight of the solution, preferably from 30 to 65 wt.-%. Optionally, the impregnated support is dried before use to form the dried catalyst system. In the dried form, the catalyst may have a concentration of phosphoric acid ranging from 5 to 55 wt.-%, preferably from 20 to 50 wt.-% based on the total weight of the dried catalyst system.

The phosphoric acid loading procedure can consist of any appropriate technique, e.g. immersion in an excess phosphoric acid solution, soaking, spray impregnation, dry impregnation, etc. The amount of solution can be equal to, larger than or smaller than the pore volume of the amount of support. Loading can be carried out at any pressure. In order to facilitate the uptake of the rather viscous phosphoric solution, the loading of the support might advantageously be carried out at subambient pressure.

The catalysts according to the invention have a very good stability against ageing under hydrothermal conditons, e.g. the conditions that are encountered during olefin hydration. If catalysts according to the invention are aged for approximately 40–45 hours at 350–370° C. in the presence of 15–18 bar water vapour, their pore size distribution is such, that the major part of the pore volume is associated with pores with a diameter smaller than 5 μm.

Changes to the pore structure of catalyst supports containing silicon dioxide under hydrothermal conditions are investigated below. Conventional unstabilised and stabilised supports are compared with the new stabilised supports.

As discussed above, the present invention also provides a process for the hydration of olefins, said process comprising reacting an olefin with water in the presence of a catalyst comprising phosphoric acid supported on a catalyst support, characterised in that said catalyst support comprises a structural framework of synthetic silica, which frame work contains domains of a particulate oxide or phosphate of at least one element selected from the group consisting of Groups IIA, IIIB, IVB, VB, VIB, VIIB, VIII, IB, IIB, IIIA, IVA and the lanthanide series of the Periodic Table; said oxide or phosphate forming 0.5 to 10 parts by weight of the total weight of the support.

Preferably, the frame work of the catalyst support contains domains of titania and/or zirconium dioxide.

The olefins to be hydrated are suitably ethylene or propylene. Where ethylene is employed, the alcohol produced is ethanol. Where propylene is employed, isopropanol and n-propanol are produced. Ethers corresponding to the olefin may also be formed as by-products during the reaction. The hydration is preferably carried out in the vapour phase, ie both the olefin and water are in the vapour phase during the reaction.

The hydration reaction is typically carried out by placing the catalyst impregnated support in a reactor, sealing the reactor and then heating the supported catalyst to the reaction temperature. The supported catalyst is preferably heated to a temperature from 170 to 300° C. depending upon the end product desired. For instance, if the end product is ethanol from ethylene, the supported catalyst is suitably heated from 225 to 280° C., preferably from 230–260° C., more preferably from 235–245° C. On the other hand, if the end product is iso-propanol and n-propanol from propylene, the supported catalyst is suitably heated from 180–225° C., preferably from 185–205° C.

When the supported catalyst bed has attained the desired temperature, a charge of the olefin and water in the vapour state may be passed through the reactor. The mole ratio of water to olefin passing through the reactor may be in the range of from 0.15 to 0.50, preferably from 0.25 to 0.45, more preferably from 0.30–0.40. The space velocity of water vapour/olefin mixture passing through the reactor may be subject to slight variations depending upon whether the reactant olefin is ethylene or propylene. For instance, in the case of ethylene, the space velocity of the mixture thereof with water vapour is suitably from 0.010 to 0.100, preferably from 0.020 to 0.050 grams per minute per cm 3 of the supported catalyst. In the case of a mixture of propylene and water vapour, the space velocity is suitably in the from 0.010–0.100, preferably from 0.02–0.07 g/min/cm3 of the supported catalyst.

The hydration reaction may be carried out a pressure ranging from 2000 to 24000 KPa. Within this range the hydration of ethylene is suitably carried out at a pressure from 3000 to 10000 KPa, whereas the hydration of propylene is suitably carried out at a pressure from 2000–7600 KPa.

BRIEF DESCRIPTION OF THE DRAWINGS

These and other aspects of the present invention will now be described, by way of illustration, with reference to the following Examples and accompanying Figures.

FIG. 9 is a graph showing how the ethanol space time yield (STY) of an olefin hydration process varies with time, depending on the catalyst employed (Example 17).

FIG. 10 is a plot of differential intrusion vs. pore diameter for a pore structure of a catalyst support stabilised with 5% of zirconia, according to this invention, after a hydrothermal ageing test (example 22).

Figure 1:
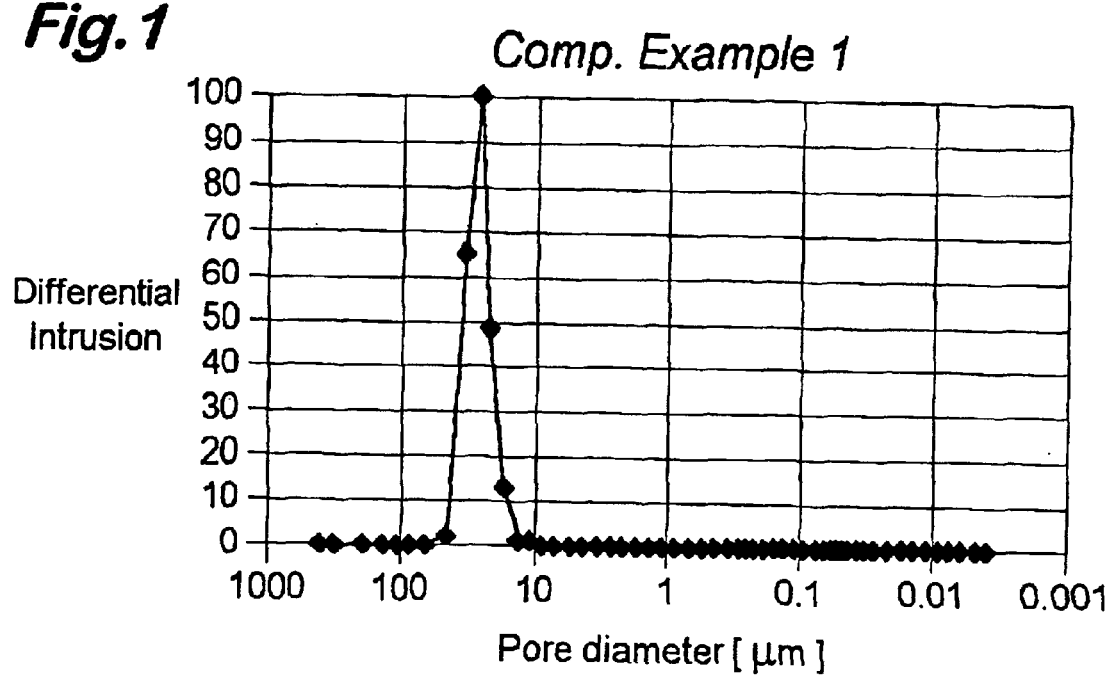
FIG. 1 is a plot of differential intrusion vs. Pore diameter for a pore structure of an unstabilised catalyst support after a hydrothermal ageing test (comp. example 1)
Figure 2:
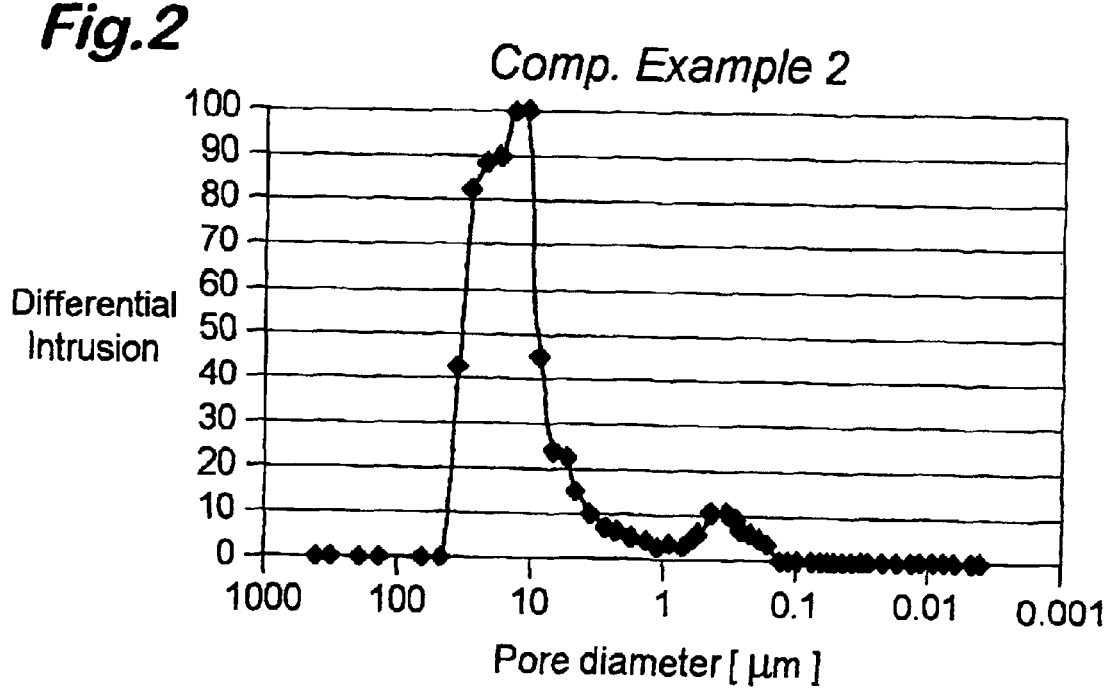
FIG. 2 is a plot of differential intrusion vs. Pore diameter for a pore structure of a catalyst support stabilised with 1.5% of titanium, according to prior art, after a hydrothermal ageing test (comp. example 2)
Figure 3:
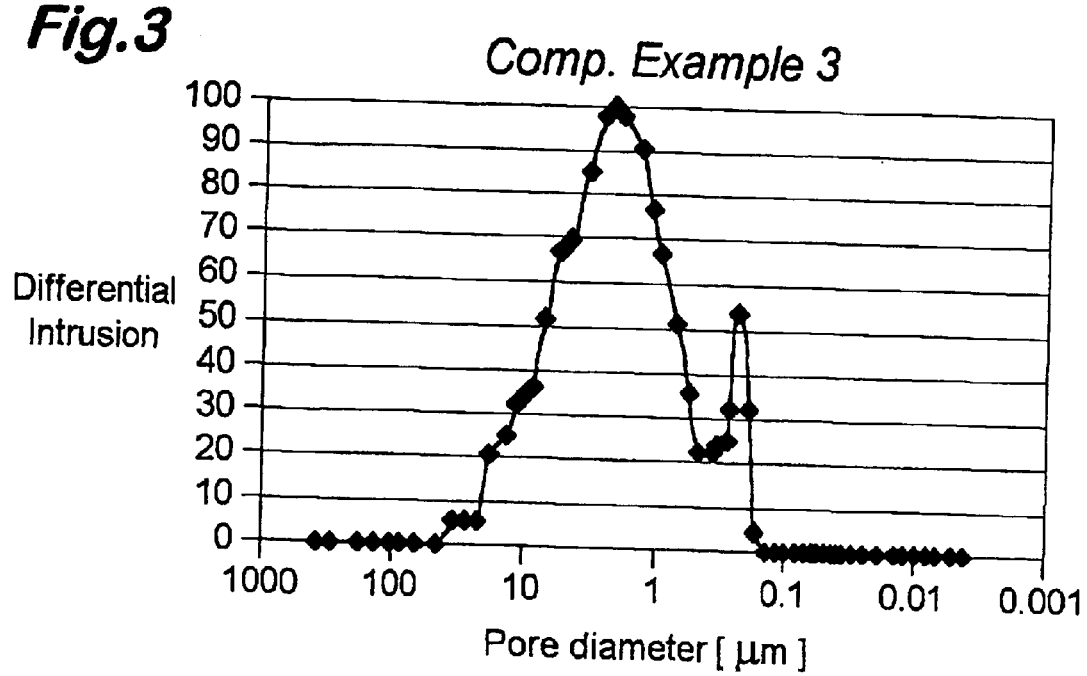
FIG. 3 is a plot of differential intrusion vs. Pore diameter for a pore structure of a catalyst support stabilised with 4% of titanium, according to prior art, after a hydrothermal ageing test (comp. example 3)
Figure 4:
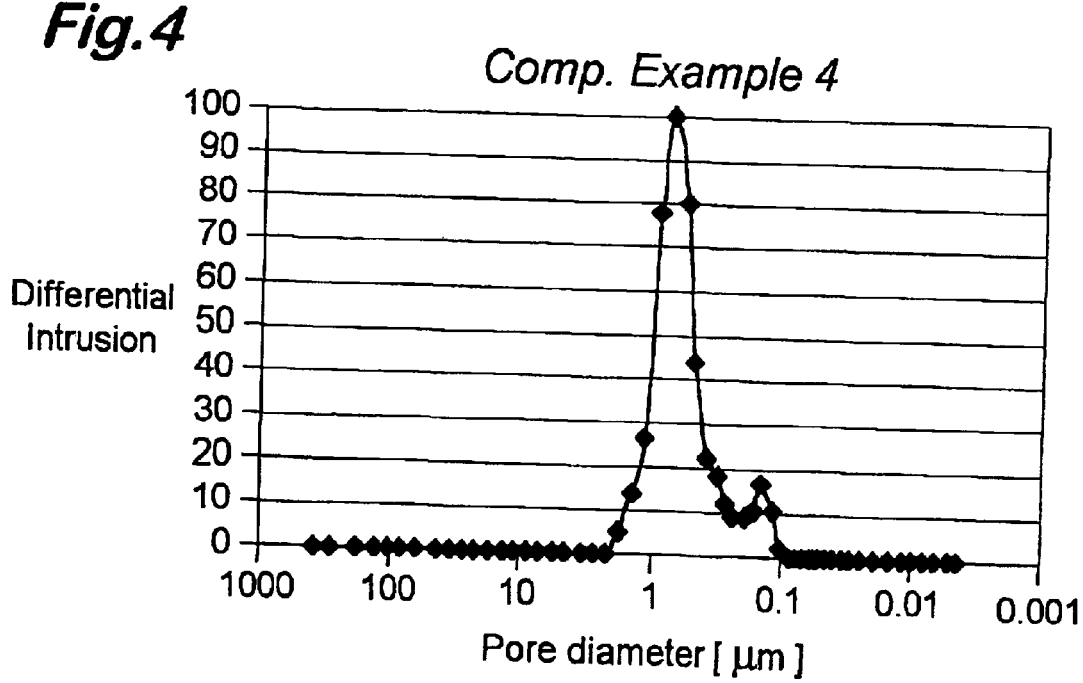
FIG. 4 is a plot of differential intrusion vs. pore diameter for a pore structure of a catalyst support stabilised with 5% of titanium, according to prior art, after a hydrothermal ageing test (comp. example 4)
Figure 5:
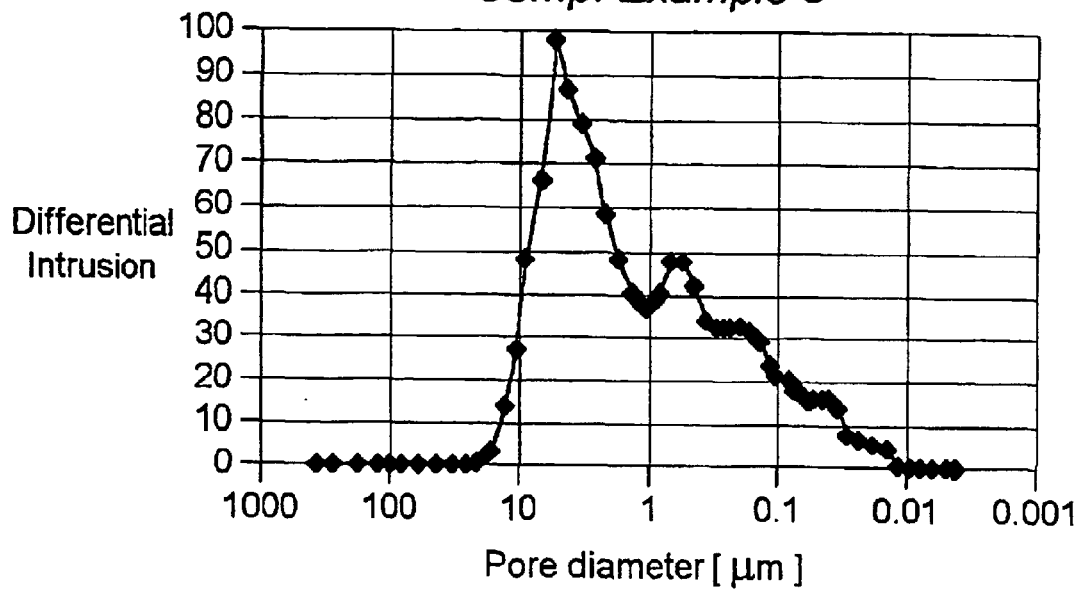
FIG. 5 is a plot of differential intrusion vs. pore diameter for a pore structure of a catalyst support stabilised with 5% of titanium, according to prior art, after a hydrothermal ageing test (comp. example 5)
Figure 6:
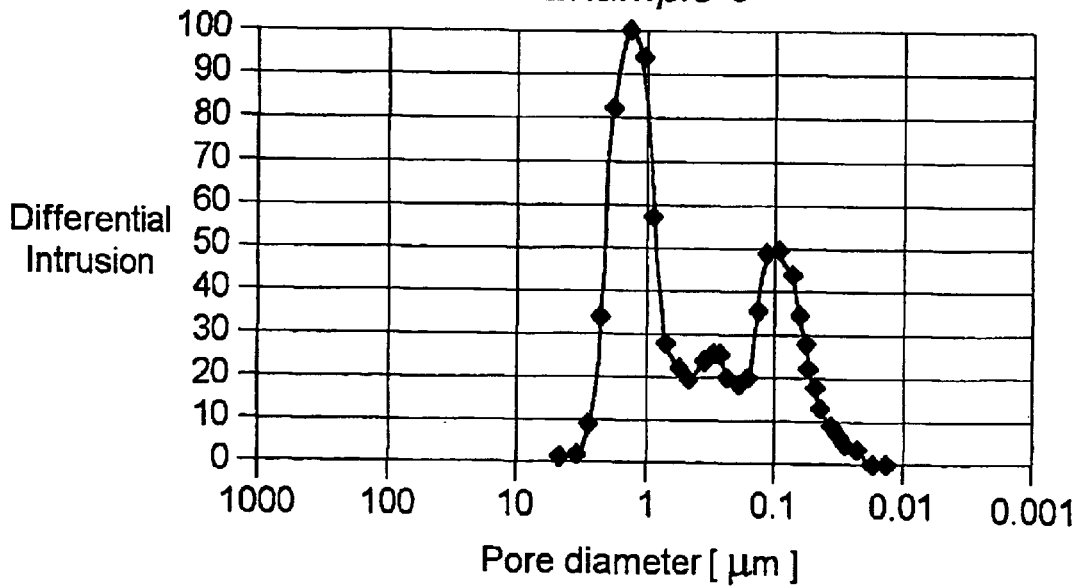
FIG. 6 is a plot of differential intrusion vs. pore diameter for a pore structure of a catalyst support stabilised with 3% of titanium, according to this invention, after a hydrothermal ageing test (example 6)
Figure 7:
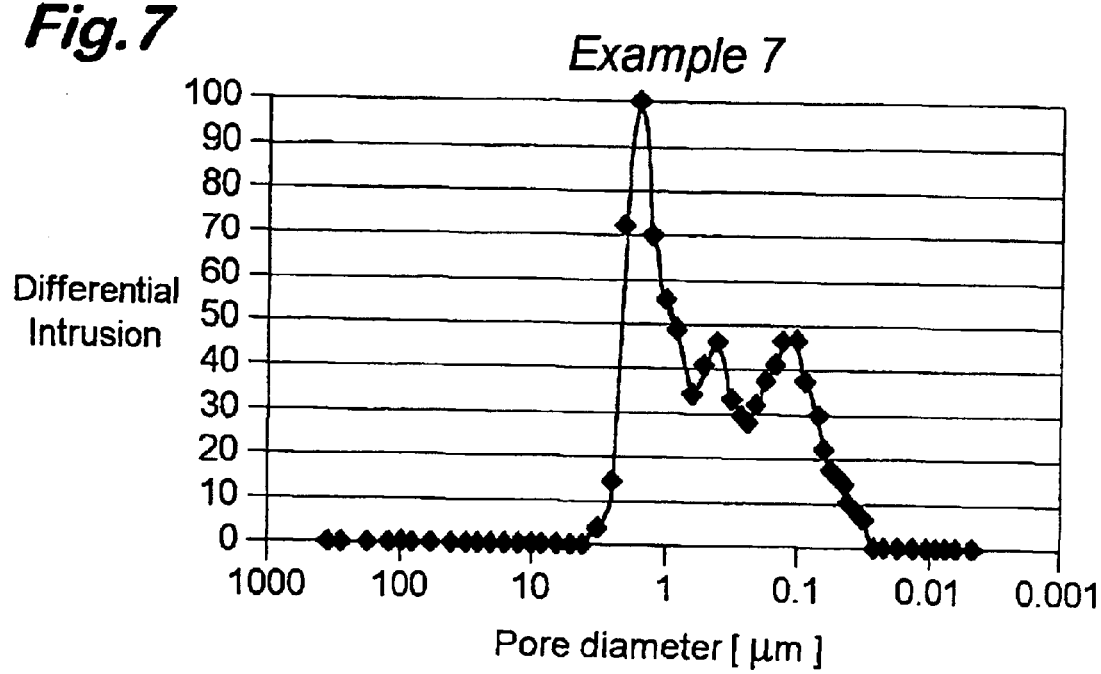
FIG. 7 is a plot of differential intrusion vs. pore diameter for a pore structure of a catalyst support stabilised with 1.8% of titanium, according to this invention, after a hydrothermal ageing test (example 7)
Figure 8:
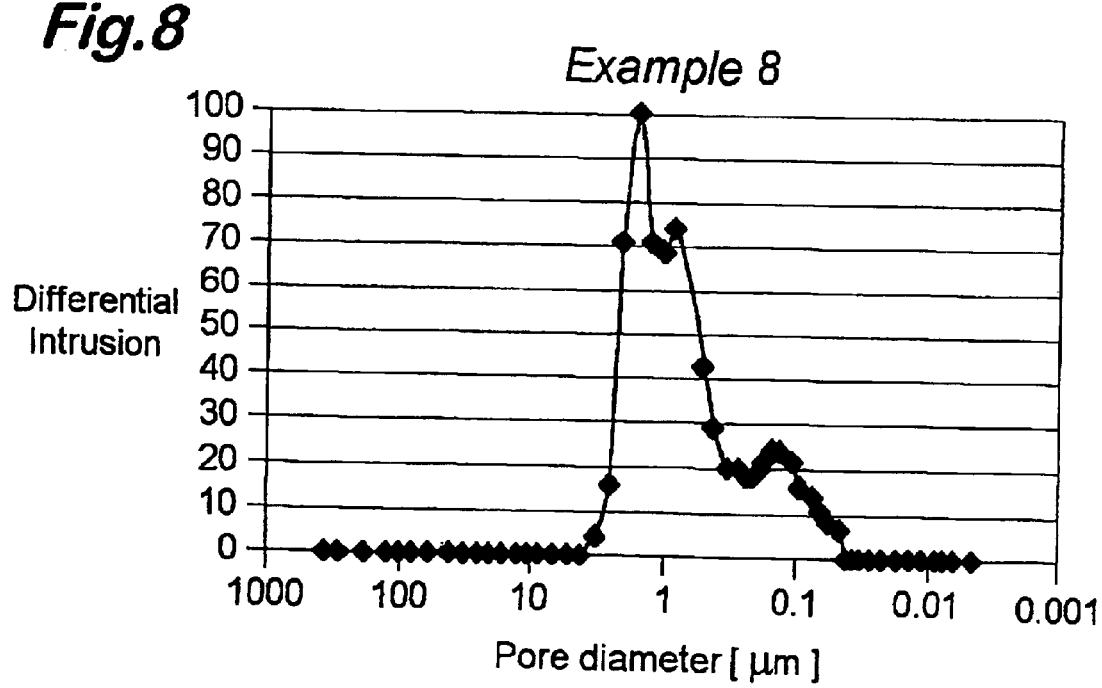
FIG. 8 is a plot of differential intrusion vs. pore diameter for a pore structure of a catalyst support stabilised with 1.8% of titanium, according to this invention, after a hydrothermal ageing test (example 8)

The pore size distribution curves shown in FIG. 1 to 8 and 10 were determined using the well-known Hg porosimetry method. They show the differential penetration (intrusion) of the mercury as a function of pore diameter. Arbitrary units were selected for differential intrusion and the curves were each expanded over the available area of the diagram.

COMPARATIVE EXAMPLE 1

A state-of-the-art support was prepared according to example 2 of EP 393 356 B1.

This support is thus made by mixing pyrogenic silica (AEROSIL®200 from Degussa-Huels), magnesiumstearate, methylcellulose and urea, and subsequent drying and tabletting. The calcination procedure consists of two steps: a first calcination at 250° C., and the final calcination at 750° C. This product is sold by Degussa-Huels under either of the names Degussa 350, Träger 350, Support 350 or Aerolyst™ 350 and has the following properties: specific surface area approx. 180 m²/g; bulk density approx. 490 g/l; total pore volume approx. 0.8 cm³/g. It consists of tablets with a diameter of 6 mm, and a height of 5.5 mm.

This support material was loaded with a 60 wt.-% phosphoric acid solution and heated to 350° C. in a high pressure apparatus at a steam pressure of 15 bar for 41 hours. The pore size distribution of the aged catalyst was determined by Hg porosimetry. The measured pore size distribution is shown graphically in FIG. 1.

The hydrothermally aged supports have a maximum in the pore size distribution at pore diameters of between 20 and 30 μm.

COMPARATIVE EXAMPLE 2

The catalyst support from comparative example 1 was modified with 1.5 wt. % of Ti. In order to modify 100 g of support with 1.5 wt. % of Ti, 33 g of a 15% titanium(III) chloride solution (TiCl₃) were diluted with water to 80 ml, corresponding to the pore volume of the support material. The support material was impregnated with this solution.

After 30 minutes exposure to the solution, the support was dried in a drying cabinet at 100° C. for 3 hours and then calcined in a furnace at 600° C. for a period of 4 hours. The support was then loaded with a 60 wt.-% phosphoric acid solution and left in a high pressure apparatus at a steam pressure of 15 bar at 350° C. for 40 hours. The pore size distribution of the aged catalyst was again determined by Hg porosimetry. The pore size distribution is shown graphically in FIG. 2.

The maximum of the pore size distribution is between 10 and 20 μm. In comparison with the undoped catalyst used in comparative Example 1, the catalyst doped with 1.5 wt. % of Ti has a higher proportion of small pores of a diameter of below 10 μm after ageing.

COMPARATIVE EXAMPLE 3

The catalyst support as described in comparative example 1 was modified with 4 wt. % of Ti. In order to modify 100 g of support with 4 wt. % of Ti, 85.93 g of a 15% titanium(II)chloride solution were diluted with water to 80 ml and distributed over the support to impregnate it.

After 30 minutes exposure to the solution, the support was dried in a drying cabinet at 100° C. for 3 hours and then calcined in a furnace at 600° C. for a period of 4 hours. The support was then loaded with a 60 wt.-% phosphoric acid solution and left in a high pressure apparatus at a steam pressure of 15 bar at 350° C. for 43 hours. The pore size distribution of this specimen is very wide. The maximum of the pore size distribution is approximately 2 μm. In comparison with the undoped catalyst used in Comparative Example 1, the catalyst doped with 4 wt. % of Ti has a high proportion of pores of a diameter of less than 10 μm. In comparison with the undoped catalyst from Comparative Example 1, the catalyst doped with 4 wt. % of Ti is distinctly more stable and the enlargement of pore diameter is distinctly less marked.

COMPARATIVE EXAMPLE 4

The catalyst support as described in Comparative Example 1 was modified with 5 wt. % of Ti. In order to modify 100 g of support with 5 wt. % of titanium, 35.5 g of tetrabutoxytitanium (Ti(C₄H₉O)₄) were diluted to 80 ml with butanol and distributed over the support. Special explosion-proof equipment was used during impregnation and drying in order to avoid any risk of explosion.

After 30 minutes exposure to the solution, the support was dried in a drying cabinet at 100° C. for 3 hours and then calcined in a furnace at 600° C. for a period of 4 hours.

The support was then loaded with phosphoric acid and heated to 350° C. in a high pressure apparatus at a steam pressure of 15 bar for 41.5 hours. The pore size distribution of the aged catalyst was determined by Hg porosimetry. The pore size distribution is shown graphically in FIG. 4.

The maximum of the pore size distribution is approximately 0.7 μm. There are virtually no pores with a diameter greater than 3 μm. In comparison with the undoped catalyst from Comparative Example 1, the catalyst doped with 5 wt. % of Ti is distinctly more stable. The average pore diameter for the catalyst doped with 5 wt. % of Ti is smaller by a factor of 35 than in the case of the undoped catalyst from Comparative Example 1.

The preparation method in this example is based on the use of an organic solvent. Industrial production of this Ti-containing support material requires the use of special explosion-proof equipment and buildings. Furthermore, large amounts of organic solvents have to be handled, and organic wastes have to be burned or otherwise recycled. This material is thus difficult to produce and, hence, expensive.

COMPARATIVE EXAMPLE 5

A similarly prepared catalyst support as described in Comparative Example 1 with a higher pore volume of 1.0 ml/g was modified with 5 wt. % of Ti by impregnation with titanylsulfate ($TiOSO_4$) which was dissolved in water that contained some $H_2O_2$. This solution was distributed over the support.

After 30 minutes exposure to the solution, the support was dried in a drying cabinet at 100° C. for 3 hours and then calcined in a furnace at 600° C. for a period of 4 hours.

The support was then loaded with phosphoric acid and heated to 350° C. in a high pressure apparatus at a steam pressure of 15 bar for 45 hours. The pore size distribution of the aged catalyst was determined by Hg porosimetry. The pore size distribution is shown graphically in FIG. 5.

In comparison with the undoped catalyst from Comparative Example 1, the catalyst doped with 5 wt. % of Ti is distinctly more stable.

EXAMPLE 6

A catalyst support in accordance with this invention was prepared by mixing 1.0 kg of pyrogenic silica (Aerosil® 200 V from Degussa-Huels, amorphous), 52.5 g of pyrogenic titania (P25 from Degussa-Huels, consisting of approx. 70–80% anatase and 20–30% of rutile, surface area 50 m²/g, $d_{50}$ 3–4 μm), 21 g of methylcellulose, 50 g of wax, 5 g of polysaccharide, 10 g of a 30% ammonia solution and 1.9 kg of water. The mixture was kneaded for approx. 30 minutes and was subsequently extruded. After drying at 110° C., the material was calcined in air at 750° C. for 3 hours. The obtained extrudates contain 5 wt.-% of $TiO_2$ and 95% of $SiO_2$. 5% $TiO_2$ corresponds to a Ti-content of 3 wt.-%. The diameter of the extrudates is 4.0 mm, the surface area is 175 m²/g, the pore volume is 0.99 ml/g, the bulk density 450 g/l and the crush strength 47 N.

The support of this example was analysed with transmission electron microscopy (TEM). The titania domains are clearly visible in the amorphous silica matrix. The titania domains have a maximum size of approximately 0.3 μm.

The support of this example was also analysed with XRD. No peaks of crystalline silica were found. Titania peaks were present for both anatase and rutile.

This support was loaded with phosphoric acid and heated to 370° C. in a high pressure apparatus at a steam pressure of 15 bar for approx. 45 hours. The pore size distribution of the aged catalyst was determined by Hg porosimetry. The pore size distribution is shown graphically in FIG. 6. There are virtually no pores of a diameter greater than 3 μm, although the Ti-content is only 3 wt.-%.

EXAMPLE 7

Another catalyst support in accordance with this invention was prepared by mixing 970 g of pyrogenic silica, 30 g of pyrogenic titania, 21 g of methylcellulose, 50 g of wax, 5 g of polysaccharide, 10 g of a 30% ammonia solution and 1.9 kg of water. The mixture was kneaded for approx. 30 minutes and was subsequently extruded. After drying at 110° C., the material was calcined in air at 850° C. for 3 hours. The obtained extrudates contain 3% of $TiO_2$ and 97% of $SiO_2$. 3% $TiO_2$ corresponds to a Ti-content of only 1.8 wt.-%. The diameter of the extrudates is 3.5 mm, the surface area is 165 m²/g, the pore volume is 1.0 ml/g, the bulk density 440 g/l and the crush strength 50 N.

This support was loaded with phosphoric acid and heated to 370° C. in a high pressure apparatus at a steam pressure of 15 bar for approx. 43 h hours. The pore size distribution of the aged catalyst was determined by Hg porosimetry. The pore size distribution is shown graphically in FIG. 7. There are virtually no pores of a diameter greater than 3 μm. In comparative example 2, the Ti-loading is 1.5 wt.-%, thus nearly identical to the Ti content of the support in this example. Comparison of the porosimetry data shows that the support of the present invention is much better stabilised. Furthermore, the support of the present invention is much easier to produce.

EXAMPLE 8

Another catalyst support in accordance with this invention was prepared by mixing 970 g of pyrogenic silica, 30 g of precipitated titania (anatase form), 21 g of methylcellulose, 50 g of wax, 5 g of polysaccharide, 10 g of a 30% ammonia solution and 1.9 kg of water. The mixture was kneaded for approx. 30 minutes and was subsequently extruded. After drying at 110° C., the material was calcined in air at 850° C. for 3 hours. The obtained extrudates contain 3 wt.-% of $TiO_2$ and 97 wt.-% of $SiO_2$. 3 wt.-% $TiO_2$ corresponds to a Ti-content of only 1.8 wt.-%. The diameter of the extrudates is 3.5 mm, the surface area is 165 m²/g, the pore volume is 1.0 ml/g, the bulk density 440 g/l and the crush strength 50 N.

This support was loaded with phosphoric acid and heated to 370° C. in a high pressure apparatus at a steam pressure of 15 bar for 43 hours. The pore size distribution of the aged catalyst was determined by Hg porosimetry. The pore size distribution is shown graphically in FIG. 8. There are virtually no pores of a diameter greater than 3.5 μm. In comparative example 2, the Ti-loading is 1.5 wt.-%, thus nearly identical to the Ti content of the support in this example. Comparison of the porosimetry data shows that the support of the present invention is much better stabilised. Furthermore, the support of the present invention is much easier to produce.

EXAMPLE 9

The most frequently applied acid loading procedure consists of soaking the support in an excess of approx. 60 wt.-% phosphoric acid solution. After this soak procedure, the excess solution is drained off and the catalyst is dried. During the soaking operation some of the titania present in the support might be dissolved. The loading procedure thus can lead to an unwanted loss of titania.

In some of the examples described above, the drained-off acid was analysed for the presence of titanium. Analysis was carried out semi-quantitatively by adding some $H_2O_2$ to the acid solution. In the presence of small amounts of titanium the solution turns yellow, higher titanium concentrations give an orange or red colour.

| Example | Colour observed |
| --- | --- |
| 1 (comparative), without Ti | none |
| 3 (comparative) | yellow |
| 4 (comparative) | orange - red |
| 5 (comparative) | orange |
| 6 | very slightly yellow |
| 7 | very slightly yellow |

As can be seen from these results, the stabilised state-of-the-art supports (examples 3, 4 and 5) suffer from substantial Ti-loss during the acid loading. The supports according to the invention do not lose any or only very little Ti. This is an advantage from the supports according to the invention.

Other advantages have been demonstrated in the previous examples: compared to the state of the art supports, they have a better or equal hydrothermal stability after loading with phosphoric acid, their method of preparation is much simpler and their titania content is lower.

EXAMPLE 10

A catalyst support according to the present invention was provided in the form of 3.5 mm cylindrical extrudates. The method employed to prepare the catalyst support of this Example is identical to that employed to prepare the catalyst support of Example 6. The Ti content of the support was 3.9% wt/wt, as measured by X-ray Fluorescence. The support had a bulk density of 480 g/l, a pore volume of 0.96 ml/g (by $H_2O$ absorption), a crush strength of 45 N (average of 50 crushed pellets, using Mecmesin crush strength tester), and a pore size distribution characterised by a sharp unimodal peak at 16 nm, as measured by Hg porosimetry.

EXAMPLE 11

A catalyst was produced by impregnating 1 litre of the support of Example 10 with phosphoric acid. This was achieved by evacuating the pores of the support to approximately 35 mmHg, and then submerging the evacuated support in a 55.3 wt/wt % solution of orthophosphoric acid (H3PO4) The support was then left to soak in the solution at atmospheric pressure for 1 hour.

After soaking, the support was filtered free of excess acid, and dried at 120° C. for 24 hours. The bulk density of the resulting catalyst was found to be 874 g/l. The acid loading of the catalyst, as calculated by subtraction of the support's bulk density, was 394 g/l.

The crush strength of the resulting catalyst was measured to be 49 N (average of 50 crushed pellets, using Mecmesin crush strength tester).

EXAMPLE 12

The catalyst of Example 11 was used to catalyse an ethylene hydration reaction. The hydration reaction was carried out in a 1 litre continuous flow pilot plant, designed to simulate the reaction section of a gas phase ethylene hydration plant. The plant was operated as follows:

Fresh ethylene gas was fed to the plant from a high pressure ethylene compressor. Liquid water was fed to the plant by diaphragm metering pump. The feeds were combined with recycled ethylene and passed through a preheater/vaporiser, before being introduced to the catalyst bed.

The catalyst was held in a copper lined tubular reactor, which was also fitted with a central multipoint thermocouple for accurately measuring catalyst temperatures at various (fixed) depths down the catalyst bed. The gaseous reactor effluent was cooled to ambient temperature using a simple shell and tube type heat exchanger, and the mixture of liquid and gaseous products were separated in a high pressure gas/liquid separator.

The gaseous product, still containing significant levels of ethanol, was then further processed in a wash tower, where the majority of the water soluble components was scrubbed out. The liquid effluent from the wash tower was then mixed with the liquid effluent from the gas/liquid separator to form the main product stream. This stream was collected and analysed (by gas chromatography).

The scrubbed gas from the wash tower was fed to a recycle compressor and returned to the reactor. The recycle gas flow rate was carefully controlled using a Coriolis meter to ensure that the contact time through the catalyst bed was similar to that employed in commercial ethanol plants. An on-line gas chromatograph was also employed to analyse the recycle stream every 15 minutes in order to determine the recycle gas composition.

The plant was operated at a pressure of 1000 psig (68 atm); a reactor inlet temperature of 240° C., a reactor exit temperature of 260° C.; a [water]:[ethylene] feed mole ratio of 0.35–0.36; a ethylene GHSV=1350 hr(−1); and a steam GHSV=485 hr (−1).

The catalyst was kept on stream for 2 weeks, during which time, the space time yields (STYs) of ethanol, ether and acetaldehyde were measured. The results are shown in Table I below.

COMPARATIVE EXAMPLE 13

A catalyst was prepared by impregnating a Degussa 350 support with phosphoric acid using an analogous method as that described in Example 11. The Degussa 350 support has been described in detail in comparative example 1. The resulting catalyst was used to catalyse an ethylene hydration reaction, using the 1 litre continuous flow pilot plant described in Example 12 above.

Table I below compares the space time yields (STY) obtained using a catalyst supported on the support of Example 10, with the STYs obtained using the phosphoric acid catalyst supported on Degussa 350 (Comparative Example 13).

TABLE I

| SUPPORT | ETHANOL STY (g/Lcat/hr) | ETHER STY (g/Lcat/hr) | ACETALDE-HYDE STY (g/Lcat/hr) | % SELECTIVITY TO EtOH |
|---|---|---|---|---|
| Comparative Example 13 | 120 | 6.35 | 0.37 | 93.6 |
| Example 10 | 136 | 6.5 | 0.45 | 94.1 |

The results show that the catalyst supported on support of Example 10 (i.e. the catalyst of Example 11) is more active and selective towards ethanol than a catalyst supported on Degussa 350 (Comparative Example 13).

EXAMPLE 14

In this Example, the pore size distribution (PSD) of the catalyst of Example 11 was measured before and after use. The fresh catalyst was found to have a pore size distribution characterised by, a sharp unimodal peak at 16 nm, as measured by Hg porosimetry. After use in the pilot plant as described in Example 12 above, the catalyst was found to be bi-modal at 165 and 380 nm.

COMPARATIVE EXAMPLE 15

Example 14 above was repeated with a catalyst supported on Degussa 350. The Degussa 350 support has been described in detail in comparative example 1. The fresh catalyst was found to have a pore size distribution characterised by a sharp unimodal peak at 17 nm, as measured by Hg porosimetry. After use, the PSD of the catalyst was found to be bimodal, with peaks at 200 nm and 3000 nm. By comparing the results of Example 14 and Comparative Example 15, it can be seen that the PSD of the catalyst of the present invention changes significantly less than the PSD of catalysts supported on titania-free supports, such as Degussa 350.

EXAMPLE 16

A catalyst support according to the present invention was provided in the form of 4 mm cylindrical extrudates. The method employed to prepare the support of this Example is identical to that employed to prepare the support of Example 6. The Ti content of the support was 4% wt/wt, as measured by X-ray Fluorescence. The support had a bulk density of 457.3 g/l, a pore volume of 1.01 ml/g (by Hg porosimetry and $H_2O$ absorption), a crush strength of 44.8 N (average of 50 crushed pellets, using Mecmesin crush strength tester), and a pore size distribution characterised by a sharp unimodal peak at 14.8 nm, as measured by Hg porosimetry.

EXAMPLE 17

A catalyst was produced by impregnating 8 litres of the support of Example 16 with phosphoric acid. This was achieved by evacuating the pores of the support to less than 40 mmHg, and then submerging the evacuated support in a 52 wt/wt % solution of orthophosphoric acid ($H_3PO_4$). The support was then left to soak in the solution at atmospheric pressure for 2 hours.

After soaking, the support was filtered free of excess acid, and dried at 120° C. for 3 days. The bulk density of the resulting catalyst was found to be 755.5 g/l. The acid loading of the catalyst as calculated by subtraction of the support's bulk density was 298.2 g/l.

The catalyst had a crush strength of 92.6 N.

EXAMPLE 18

The catalyst of Example 17 was used to catalyse an ethylene hydration reaction. The hydration reaction was carried out in an 8 litre continuous flow pilot plant, designed to simulate the reaction section of a gas phase ethylene hydration plant. The plant was operated as follows:

Fresh ethylene gas was fed to the plant from a high pressure ethylene compressor. Liquid water was fed (by diaphragm metering pump) into a "drip-feed" vaporiser, which converted the liquid water into steam. The feeds were then combined with recycled ethylene, and passed through the catalyst bed.

The catalyst was held in a copper lined tubular reactor, which was also fitted with a central multipoint thermocouple for accurately measuring catalyst temperatures at various (fixed) depths down the catalyst bed. The gaseous reactor effluent was cooled to ambient temperature using a simple shell and tube type heat exchanger. The mixture of liquid and gaseous products were separated in a high pressure gas/liquid separator. The gaseous product, still containing significant levels of ethanol, was then further processed by passing it through a wash tower. In the wash tower, the majority of the water soluble components was removed from the gaseous product.

The liquid effluent from the wash tower was then mixed with the liquid effluent from the gas/liquid separator to form the main product stream. This stream was collected and analysed (by gas chromatography) on a regular basis to provide catalyst activity and selectivity data.

The scrubbed gas from the wash tower was fed to a recycle compressor and returned to the reactor. The recycle gas flow rate was carefully controlled using a Coriolis meter to provide a similar contact time through the catalyst bed as that encountered in commercial ethanol plants. An on-line gas chromatograph was also employed to analyse the recycle stream.

The plant was operated at a 1000 psig (68 atm) pressure, a reactor inlet temperature of 240° C., a reactor exit temperature of 265° C.; a [water]:[ethylene] feed mole ratio of 0.28–0.30; a typical ethylene GHSV of 1250 $hr^{(-1)}$; and a typical steam GHSV of 357.6 $hr^{(-1)}$.

The catalyst was kept on stream for 2 weeks, during which time the ethylene STY of the process was measured 20 times, at regular test intervals. The results are shown in FIG. 9 below.

As can be seen from the graph of FIG. 9, the catalyst of Example 17 is significantly more active than prior art catalysts, such as phosphoric acid supported on Degussa 350 (Comparative Example 13).

In fact, the performance of Example 17 is comparable to that of a catalyst supported on a conventional silica gel, such as Grace 57 in terms of spot productivity. However, as shown by the results of Example 19 and Comparative Example 20 (below), the catalyst of Example 17 is considerably superior to Grace 57 in terms attrition resistance.

After use, the pellet crush strength of the catalyst was found to have improved from 92.6 N (fresh catalyst) to 169.4 N (used catalyst). This compares favourably to the crush strengths of catalysts supported on Degussa 350, which have fresh and used crush strengths of 77 N and 148 N, respectively.

The pore size distribution (PSD) of the used catalyst of Example 17 was also found to be different to that of the fresh catalyst. After one pilot run, the used support was found to be broad uni-modal at 171 nm. Although the PSD of the support had opened up, this was not to the same degree as prior art supports such as Degussa 350. After use, Degussa 350 supports were found to be bimodal at 200 nm and 3000 nm.

EXAMPLE 19

Attrition resistance of the catalyst of Example 17 was quantified by measuring the amount of dust/broken pellets (fines) generated before and after use.

When the fresh catalyst was sieved through a 2 mm sieve, and the collected fines weighed on an analytical balance, only 0.05% wt fines were found to have been generated.

After a 2 week run, the catalyst was sieved through a 2 mm sieve. The collected fines were weighed on an analytical balance. Only 0.6% wt fines had been generated (some of which by the act of removing the catalyst from the reactor, and not by the process).

COMPARATIVE EXAMPLE 20

In this Example, the attrition resistance of a phosphoric acid catalyst supported on a silica gel (Grace 57) support was measured using the process of Example 19. After a 2 week run, the silica gel catalyst was sieved through a 2 mm sieve. The collected fines were weighed on an analytical balance. 10 wt % fines had been generated.

A comparison of the results of Example 19 and Comparative Example 20 shows that the catalyst of Example 18 is considerably superior to Grace 57 in terms of attrition resistance.

EXAMPLE 21

Since titanium is added to the catalyst support to stabilise the support's physical structure, it is important that the titanium is not lost from the support when subjected to process conditions. Hence, samples of the used catalyst of Example 18 were analysed for Ti content using X-ray Fluorescence. The results were compared to the Ti content of the unused catalyst. It should be noted that the used catalyst was subjected to Soxhlet extraction prior to analysis in order to remove the orthophosphoric acid catalyst, and any dissolved titanium.

The titanium content of the support has marginally decreased from 4.0 to 3.8% wt/wt in the first run. However, the used catalyst has retained ca. 3% phosphorus, and the bulk density of the support changes as a result. When this is taken into account, there is no evidence for any Ti loss from the support (to within the accuracy of the XRF technique).

In addition, there was no evidence for Ti leaching during catalyst preparation and operation.

EXAMPLE 22

A catalyst support in accordance with this invention was prepared by mixing 1.0 kg of pyrogenic silica (Aerosil® 200 V from Degussa-Huels, amorphous), 60 g of zirconium hydroxide, 20 g of methylcellulose, 50 g of wax, 5 g of polysaccharide, 10 g of a 30% ammonia solution and 1.85 kg of water. The mixture was kneaded for approx. 30 minutes and was subsequently extruded. After drying at 110° C., the material was calcined in air at 850° C. for 3 hours. The obtained extrudates contain 5 wt.-% of $ZrO_2$ and 95% of $SiO_2$ wt.-%. The diameter of the extrudates is 4.0 mm, the pore volume is 0.97 ml/g, the bulk density 460 g/l and the crush strength 58 N.

This support was loaded with phosphoric acid and heated to 370° C. in a high pressure apparatus at a steam pressure of 15 bar for approx. 45 hours. The pore size distribution of the aged catalyst was determined by Hg porosimetry. The pore size distribution is shown graphically in FIG. 10. Substantial part of the pores has a diameter smaller than 5 $\mu$m.

Further variations and modifications of the foregoing will be apparent to those skilled in the art and are intended to be encompassed by the claims appended hereto.

What is claimed is:

1. A process for the hydration of olefins, said process comprising reacting an olefin with water in the presence of a catalyst comprising phosphoric acid supported on a catalyst support, said catalyst support comprising synthetic silica and 0.5–10 parts by weight of an oxide or phosphate of at least one element selected from Group IIA, IIIB, IVB, VB, VIB, VIIB, VIII, IB, IIB, IIIA, IVA and the lanthanide series of the Periodic Table, wherein the catalyst support is obtainable by mixing particulate synthetic silica with a particulate oxide, phosphate or oxide or phosphate precursor of at least one element selected from Groups IIA, IIIB, IVB, VB, VIB, VIIB, VIII, IB, IIB, IIIA, IVA and the lanthanide series of the Periodic Table, forming a catalyst support from the resulting mixture, and calcining the resulting catalyst support.

2. A process as claimed in claim 1, wherein the catalyst support comprises synthetic silica and 0.5–10 parts by weight of titania and/or zirconium dioxide, and is obtainable by mixing particulate synthetic silica with particulate titania, zirconium dioxide and/or precursors thereof, forming a catalyst support from the resulting mixture, and calcining the resulting catalyst support.

3. A process as claimed in claim 1, wherein the content of synthetic silica in the calcined support is at least 80%.

4. A process for the hydration of olefins, said process comprising reacting an olefin with water in the presence of a catalyst comprising phosphoric acid supported on a catalyst support, wherein said catalyst support comprises a structural framework of synthetic silica, which framework contains domains of a particulate oxide or phosphate of at least one element selected from the group consisting of Groups IIA, IIIB, IVB, VB, VIB, VIIB, VIIIB, IB, IIB, IIIA, IVA and the lanthanide series of the periodic Table; said oxide or phosphate forming 0.5 to 10 parts by weight of the total weight of the support.

5. A process as claimed in claim 4, wherein the frame work of the catalyst support contains domains of titania and/or zirconium dioxide.

6. A process as claimed in claim 4, wherein the framework of the catalyst support contains domains of titania and/or zirconium dioxide and at least 50% of the titania and/or zirconium dioxide domains in the calcined support are smaller than 0.8 $\mu$m.

7. A process as claimed in claim 1, wherein the synthetic silica comprises pyrogenically produced silica.

8. A process as claimed in claim 2, wherein the titania comprises pyrogenically produced titania.

9. A process as claimed in claim 1, wherein the calcining step is carried out between 400 and 1050° C.

10. A process as claimed in claim 1, wherein the catalyst contains 5–55 wt.-% of phosphoric acid, based on the total weight of the dried catalyst.

11. A process as claimed in claim 1, wherein said olefin is ethylene or propylene and wherein the reaction between said olefin and water is carried out at a temperature of 170 to 300° C.

12. A process as claimed in claim 1, wherein the mole ratio of water to olefin employed is in the range of from 0.15 to 0.50.

* * * * *